United States Patent [19]

Girard, Jr.

[11] Plant 5,014

[45] Mar. 29, 1983

[54] JUNIPER PLANT

[76] Inventor: Peter E. Girard, Jr., P.O. Box 428, Geneva, Ohio 44041

[21] Appl. No.: 189,684

[22] Filed: Sep. 22, 1980

[51] Int. Cl.[3] ..... A01H 5/00
[52] U.S. Cl. ..... Plt./50
[58] Field of Search ..... Plt./50

[56] References Cited

PUBLICATIONS

Girard, P., "Juniperus Chinensis", *Girard Nurseries, 1982 Catalog*, p. 13, (only), (publisher unknown).
Harrison, C. R., "Juniperus", *Ornamental Conifers*, Pub.: Hafner Press, 1975, pp. 99 and 100 (only).

*Primary Examiner*—James R. Feyrer
*Attorney, Agent, or Firm*—Baldwin, Egan, Walling & Fetzer

[57] ABSTRACT

A new and distinct juniper branch was discovered, from which a number of cuttings were made and rooted, said branch being discovered on an unpatented variety of (parent) juniper plant identified as Juniperus × Media.

1 Drawing Figure

SUMMARY OF THE INVENTION

My invention relates to a new and distinct variety of juniper plant which was discovered by me as a branch of a juniper × media (parent) plant, on Dec. 20, 1965, at Girard Nurseries Property; (U.S. Route 20), 6839 North Ridge East, Saybrook Township, Geneva, Ohio. Such branch was discovered growing from a heavy side branch of a thirty-five year old, eight feet wide, four feet tall, juniperus × media (parent) plant which I originally planted, such parent plant growing in a row of (planted variety) golden pfitzer junipers. The aforesaid parent plant was observed continuously for many years.

The juniper plant of the invention (commercially known as Juniperus × media Saybrook Gold) was asexually reproduced from cuttings at Girard Nurseries, U.S. Route 20, Geneva, Ohio, under the environment of greenhouse conditions, under glass, with a humidity of 60% to 70% in fall and winter weather with shading delayed until spring.

My discovery differs from other juniper plants in that it has a much brighter yellow color than any other juniper plants observed and it has a very dense and compact growing habit. Its height is about thirty-two inches and its width is about forty inches. It has needle-type leaves on shoots and has a distinct compact habit of growth. More specifically, the plant of the invention differs from other commercial varieties of similar type such as "Gold Coast", "Old Gold" and "Golden Pfitzer" in that it has a much deeper, brighter and more intense yellow color which is retained throughout the four seasons, and its growing habit is unusually dense and compact in comparison with the above-mentioned commercial varieties and in comparison with any other similar type of juniper plant. It is to be particularly noted that the present plant of the invention retains its very bright yellow color throughout the winter season as well as in the spring, summer, and fall seasons, such characteristic being devoid in other juniper plants. Also, it is to be noted that the intense yellow color of the present plant substantially dominates the plant in that such bright yellow color is dominate in a majority of the leaves and branches, such being in clear distinction to the above-mentioned commercial varieties wherein only the tips of the foliage are yellow.

Although the juniper plant of my invention is not a vigorous growing plant, it fills out and makes up into an ideal specimen in a relatively short time, and is a relatively low-growing plant, with graceful branches, drooping at tips.

The present variety plant has its brightest color in the outer exposed areas that can be seen, and in the areas where little or no light is received (and in the center of the plant) the color is a greenish-yellow or chartreuse.

The new variety retains its pleasant coloration throughout the year and due to its small size and rather slow growth, the plant is ideal for tub use or it may be planted in containers. The new variety is ideally suited wherever a compact low evergreen plant is required.

BRIEF DESCRIPTION OF THE DRAWINGS

The accompanying drawing, in full color, shows a typical specimen of the entire plant of my new discovery as close to the natural colors as can be reproduced by this method.

The following is a detailed description of the new and distinct variety. To assist in the identification of the important colors, the nomenclature adopted by The Royal Horticultural Society Colour Charts (R.H.S.) has been followed.

THE PLANT

Type: Evergreen ornamental shrub, juvenile, needle-shaped.

Parentage: Juniperus × media.

Growth habit: The plant has compact and low growth habit. When viewed from above, it has a bright golden cushion appearance that is round and slightly irregular.

Size:

Height is about 32 inches.
Width is about 40 inches.

Foliage:

Juvenile foliage is ¼ inch to ⅜ inch long and slightly tapered.

The foliage is needle-shaped, with new foliage being soft to touch; older needles are somewhat sharp. There is only one type of leaf.

Summer color is vivid yellow; R.H.S. 9A yellow. Reverse side or beneath, R.H.S. 154B yellow green.

Winter color is a deeper shade of yellow, specifically R.H.S.-15B yellow-orange. Reverse side, R.H.S.-1A green-yellow.

The leaves are arranged or formed along the stems or branches opposite each other.

Branches:

*Summer color.*—The summer color of growing tips of the main branches and side shoots are smooth vivid yellow, color R.H.S.-9A yellow, deepening to a vivid deeper shade R.H.S.-124 yellow. Color of secondary branches are vivid R.H.S. 9A yellow as branches mature. All not receiving sunlight or in semi-shade, take on a strong R.H.S.-154A yellow-green.

*Winter color.*—Winter color is a deeper vivid color, R.H.S.-9A yellow. Tips along with side branches remain the same in winter.

The branches tend to have a horizontal habit with graceful descending tips and not generally upright.

Spread of plant: A ten year old plant will have an average spread of 4 feet. It is more branched at the base than usual and has restrained spreading.

Height of plant: The height of the plant averages 2½ to 3 feet in ten years.

Growth habit: It grows more compact and develops uniformity more quickly than other juniper plants observed. It is a relatively slow grower, but not a dwarf. It will grow 8 to 10 inches a year. The new plants grow compact, and make up readily.

Hardiness: It is very hardy and has performed well at 22° below zero Fahrenheit with no winter injury. It is apparent that it will withstand 35° to 45° below zero Fahrenheit with a maximum wind-chill factor of 70° below zero Fahrenheit. The plant is also very summer hardy with the highest summer temperature of exposure being 105° Fahrenheit.

Changes when sunlight is decreased: If a considerable amount of direct sunlight is decreased the yellow may become deeper in color, and takes on some greenish tints (R.H.S.-154 yellow-green). When grown in the shade, depending on the amount of shade, there may be some losses in the yellow color, turning in color into a chartreuse, or R.H.S.-1A yellow-green.

Propagation: The plants are propagated by cuttings; 4 to 6 inch scions are taken from the mother plant, dipped in buteric acid and placed in sand. This plant cannot be reproduced from seed.

Insect and disease problems:

No insect or disease problems have been experienced except for the usual scale and mites that attack most all types of junipers.

No root problems or root rot have been experienced.

No trouble with water mold fungus has been experienced.

Production methods: The plant lends itself well to field growing, automatic machine potting, transplanting in close rows, and all cultural practice known to the growers. It will grow in heavy clay soil, and light sandy soil (of pH 4.5 to pH 7). It grows well in soilless composts. It can easily be grown in containers as it is a great container plant and enhances its beauty and value when grown by this method.

Pruning and trimming: Since this plant is not a wild, vigorous grower, very little shearing is required.

Descendants true? Being a sport, the plant's descendants are true and well established. The strain and its offspring are true in all habit of growth and color.

Fruit, blooms, seeds and cones: The plant has no fruit, blooms, seeds or cones up to the present time.

Genus: Juniperus × media Saybrook Gold

Genus of parent: Juniperus × media (parent not patented).

cm I claim:

1. A new and distinct variety of juniper plant substantially as herein shown and described characterized particularly as to novelty by the unique combination of its distinctive and unique dense compact low habit of growth and quick uniformity whereby very little if any pruning or trimming is required, its unusually intensely bright and attractive yellow color which it retains throughout the four seasons of the year, the foliage reverse side being a yellow green, the intense yellow color substantially dominating the entire plant, its unusual hardiness under extreme weather conditions, its relatively dense and profuse scale-like and needle-like foliage, its disease and pest resistance, its unusual ability to lend itself to accepted production methods, technics and cultural practices of field-grown nursery stocks, and by its absence of fruit, blooms, seeds and cones.

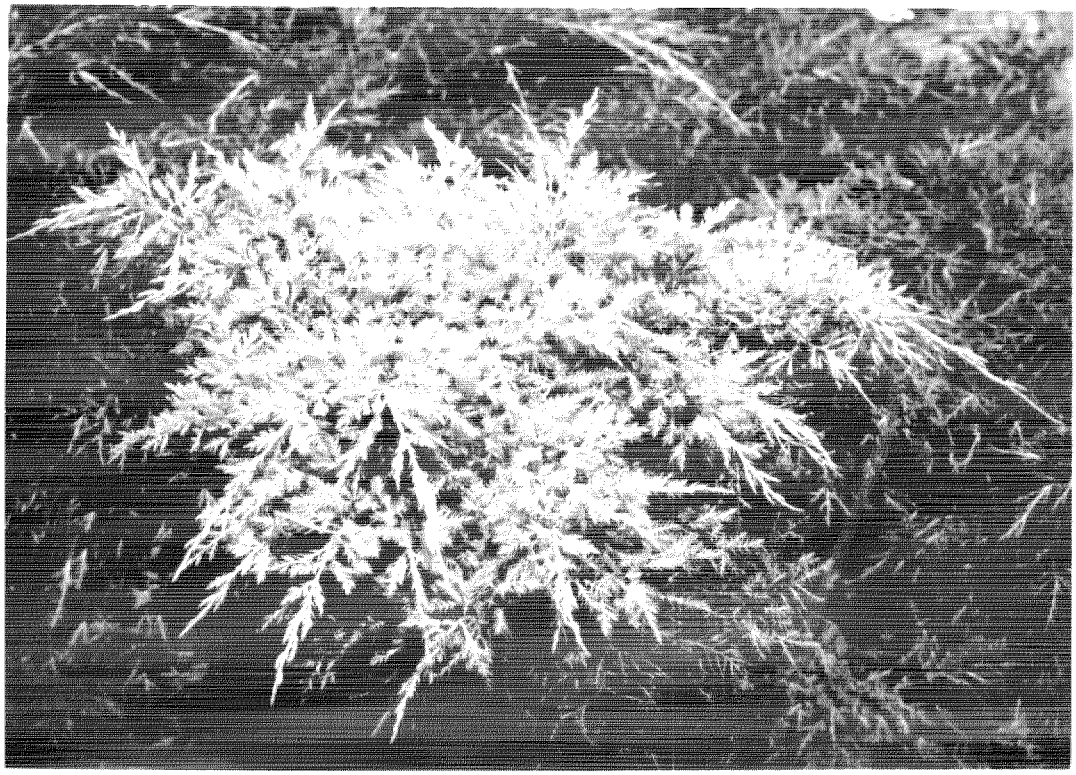

* * * * *